US008154718B2

(12) United States Patent
Graf et al.

(10) Patent No.: US 8,154,718 B2
(45) Date of Patent: Apr. 10, 2012

(54) APPARATUS AND METHOD FOR INSPECTING MICRO-STRUCTURED DEVICES ON A SEMICONDUCTOR SUBSTRATE

(75) Inventors: Uwe Graf, Solms (DE); Lambert Danner, Wetzlar-Naunheim (DE)

(73) Assignee: Vistec Semiconductor Systems GmbH, Wetzlar (DE)

( * ) Notice: Subject to any disclaimer, the term of this patent is extended or adjusted under 35 U.S.C. 154(b) by 53 days.

(21) Appl. No.: 11/568,949

(22) PCT Filed: May 23, 2005

(86) PCT No.: PCT/EP2005/052351
§ 371 (c)(1),
(2), (4) Date: Nov. 10, 2006

(87) PCT Pub. No.: WO2005/124422
PCT Pub. Date: Dec. 29, 2005

(65) Prior Publication Data
US 2007/0247618 A1     Oct. 25, 2007

(30) Foreign Application Priority Data
Jun. 16, 2004   (DE) .................. 10 2004 029 212

(51) Int. Cl.
*G01N 21/00*  (2006.01)
(52) U.S. Cl. .................. 356/237.5; 356/239.3
(58) Field of Classification Search .... 356/237.2–237.5, 356/237.4, 239.1, 239.3, 239.7–239.8; 359/368, 359/385
See application file for complete search history.

(56) References Cited

U.S. PATENT DOCUMENTS

| 4,148,552 | A |   | 4/1979  | Suzuki et al. |
|-----------|---|---|---------|---------------|
| 5,197,105 | A | * | 3/1993  | Uemura et al. ............... 382/147 |
| 5,493,236 | A | * | 2/1996  | Ishii et al. .................... 324/752 |
| 6,404,545 | B1|   | 6/2002  | Ishiwata |
| 6,587,193 | B1|   | 7/2003  | Reinhron |
| 2001/0030744 | A1| * | 10/2001 | Chang .................... 356/237.3 |
| 2002/0067477 | A1| * | 6/2002  | Morita et al. ............. 356/237.5 |
| 2002/0113210 | A1|   | 8/2002  | Treado et al. |
| 2003/0202178 | A1|   | 10/2003 | Tsuji |

FOREIGN PATENT DOCUMENTS

EP     455857       11/1991
EP     0539609 A    5/1993

OTHER PUBLICATIONS

Sartorius B. et al. Wavelength selectrive infrared microscopy . . . Journal of Applied Physics USA, Nov. 15, 1986, pp. 3401-3406, v.60, No. 10, American Institute of Physics, USA.

* cited by examiner

*Primary Examiner* — Tarifur Chowdhury
*Assistant Examiner* — Michael P Lapage
(74) *Attorney, Agent, or Firm* — Houston Eliseeva, LLP

(57) ABSTRACT

Previously used examination devices and methods mostly operate with reflected visible or UV light to analyze microstructured samples of a wafer (38), for example. The aim of the invention is to increase the possible uses of said devices, i.e. particularly in order to represent structural details, e.g. of wafers that are structured on both sides, which are not visible in VIS or UV because coatings or intermediate materials are not transparent. Said aim is achieved by using IR light as reflected light while creating transillumination (52) which significantly improves contrast in the IR image, among other things, thus allowing the sample to be simultaneously represented in reflected or transmitted IR light and in reflected visible light.

12 Claims, 1 Drawing Sheet

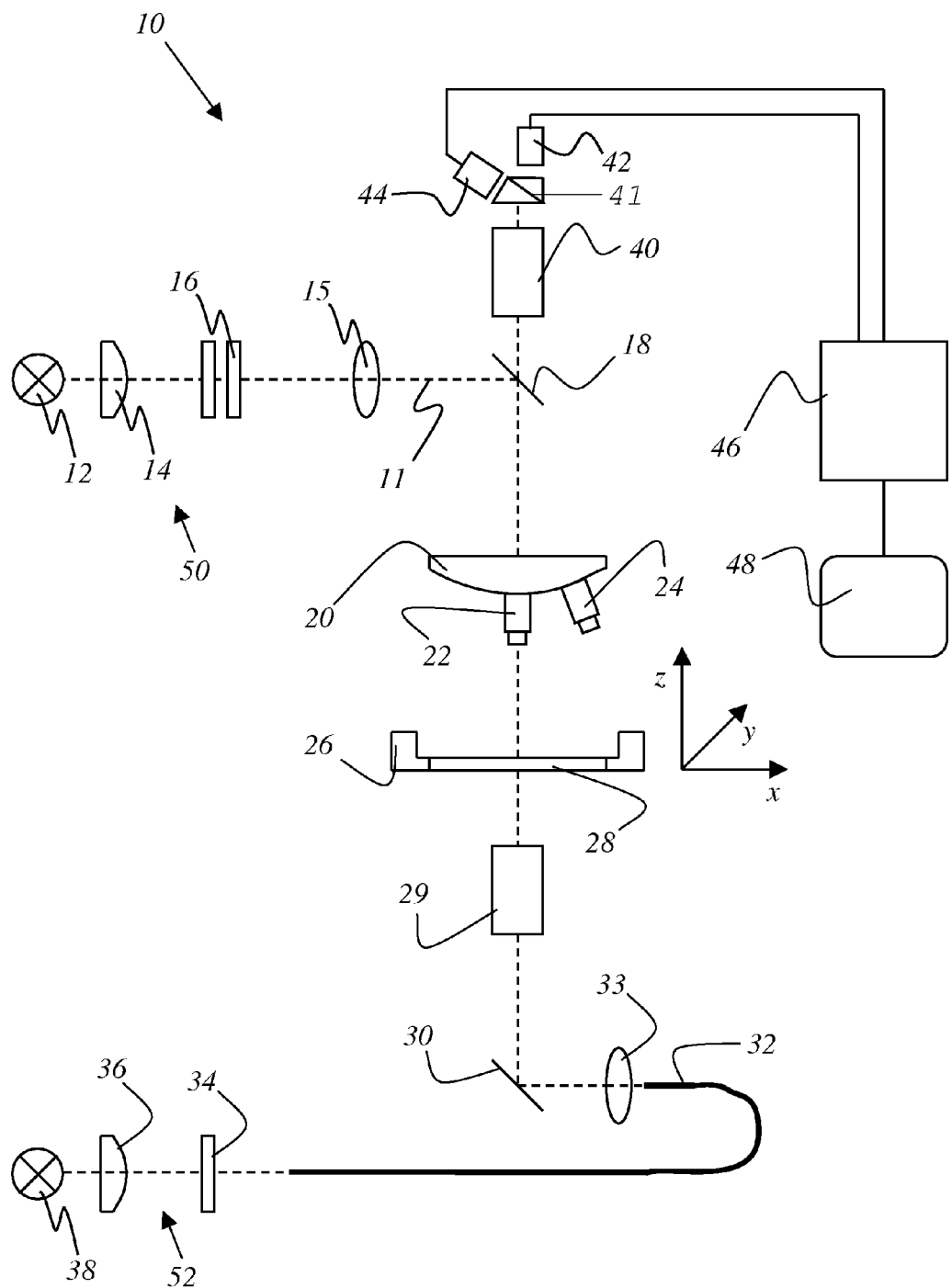

APPARATUS AND METHOD FOR INSPECTING MICRO-STRUCTURED DEVICES ON A SEMICONDUCTOR SUBSTRATE

RELATED APPLICATIONS

This application is a National Stage application of PCT application serial number PCT/EP2005/052351 filed on May 23, 2005 which in turn claims priority to German application serial number 10 2004 029 212.4 filed on Jun. 16, 2004.

FIELD OF THE INVENTION

The present invention relates to apparatus for the optical inspection of micro-structured samples, comprising a sample support on which the sample can be placed for inspection, and to a method of optically inspecting micro-structured samples, wherein a sample support is provided, on which the sample is placed for inspection, and an observation means, in particular a microscope, with which the sample is observed.

BACKGROUND OF THE INVENTION

For inspecting the surface of micro-structured samples, such as wafers, masks or micro-structured devices on a substrate, optical apparatus are particularly suitable. For example as known from EP 455 857 the inspection of the surface can be carried out by evaluating beams retro-reflected from the surface of the wafer.

Optical apparatus are also known in which various structures on the surface of the sample of a wafer can be recognized by means of image detection. Herein the sample is usually illuminated in the bright field and sampled with a camera, such as a matrix or linear array camera.

The inspection of the surface of a wafer is also known from U.S. Pat. No. 6,587,193, wherein an illumination is chosen which samples the wafer in the form of a line. The illumination line is scanned across the surface of the wafer in such a way that a two-dimensional image can be created.

From US 2003/0202178 A1, furthermore a method and an apparatus for inspecting a wafer are known. Herein an illumination is radiated onto the wafer in such a way that it is incident on an edge of the wafer. The edge of the wafer can thus be detected and further processed by an image processing unit. Defects on the wafer can be detected by comparing the obtained edge image with a prestored reference image.

The prior art systems for inspecting wafers are almost exclusively designed for the incident-light inspection in the visual or UV ranges, and are generally not or not well suited for the inspection of micro-structured samples, such as encapsulated or embedded objects or wafers structured on both sides, and stacked structures of a plurality of wafers.

SUMMARY OF THE INVENTION

It is therefore an object of the present invention to further develop the conventional sample inspection technology so that it is also suitable for the inspection of encapsulated or embedded objects or wafers structured on both sides, as well as of stacked structures of a plurality of wafers.

According to the invention the present object is achieved by an apparatus for inspecting micro-structured samples having the features according to claim 1, and a method of inspecting micro-structured samples having the features according to claim 9.

According to the present invention, also an inspection apparatus, in particular a microscope is suggested, which enables simultaneous or separate incident and transmitted-light illumination of the samples in the IR spectral range, and also realizes visual incident-light illumination.

In order to achieve a high-contrast image, in a preferred embodiment, the incident-light illumination includes an incident-light source and a filtering means for filtering radiation from the optical spectral range.

As an illumination means for the transmitted-light apparatus, a light source can be used which emits radiation with components from the infrared spectral range (IR). Together with exchangeable filters for wavelength selection, the desired wavelength is selectable. The light is preferably coupled into the system via a light guide. Through this diverse illumination with incident light and transmitted light it becomes possible to combine the advantages of IR illumination with those of the visual incident-light illumination. In the transmitted-light mode, IR light is transmitted by the sample only in those places which are transparent to it. The result is an image very high in contrast. The incident-light illumination in the IR, which is simultaneously possible, enables the imaging of objects which are usually impossible to image in the transmitted-light mode due to shadowing by metalized layers. In combination, an image rich in detail and high in contrast is created having structures which in the visual incident light are not visible due to the lack in transparency of many layers. At the same time, however, the usual visible incident-light image is available for orientation purposes. Both images, i.e. the combined incident and transmitted-light IR image and the visual incident-light image can be imaged via a wavelength selective video double output simultaneously onto an IR special camera and onto a normal visual color or monochromatic CCD camera and displayed on a monitor via a computer. This functionality can be further improved in that the light wavelengths used are adjustable, wherein in particular exchangeable filters are used for the incident and transmitted-light illumination.

The apparatus can also be further improved by the use of switchable diaphragms in the beam path of the incident and transmitted-light illumination.

The detection of the images of the samples is carried out depending on the adjusted wavelength with conventional objectives and tube lenses or via IR objectives, in particular via special IR objectives corrected depending on the sample thickness, and special IR tube lenses.

By using an autofocus system for focusing on the sample, wafer, mask or substrate with micro-structured components, the overall system can be automized, which is advantageous in particular with the in-line utilization in the production of wafers. With the aid of a PC, the images of the incident and transmitted-light system can be combined in such a way that they can be output together on an output apparatus, in particular a monitor.

BRIEF DESCRIPTION OF THE DRAWINGS

Further advantages and an advantageous embodiment of the invention are the subject matter of the annexed single FIGURE and the portion of the description relating to it, in which:

The FIGURE schematically shows a wafer inspection apparatus in an overview.

DETAILED DESCRIPTION OF THE PREFERRED EMBODIMENTS

The single FIGURE schematically illustrates a characteristic structure according to the present invention, of a wafer inspection apparatus 10, in particular a microscope for observing a wafer 28. The term wafer inspection apparatus 10 should not be construed, however, as a limitation of the invention. With the aid of wafer inspection apparatus 10, micro-structured samples, such as wafers, masks or micro-structured devices (encapsulated or unencapsulated) on a substrate (usually a semiconductor substrate) can be inspected. The wafer inspection apparatus 10 has an incident-light illumination means 50. It essentially comprises an incident-light source 12 having its light directly or indirectly coupled onto wafer 28. For this purpose, the incident-light beam 11 can be passed through a collector 14. With the subsequent arrangement of one or more exchangeable filters 16, the light wavelength desired for illumination can be filtered from the optical spectral range. Furthermore, a switchable diaphragm 15 can also be provided, to select from the incident-light beam 11 the portion desired for illuminating wafer 28. The incident-light beam can then be directed by means of a beam-splitting mirror 18 onto wafer 28, which is fixed on a substrate support 26. The light of incident-light source 12 can, of course, also be directly coupled in, such as with the aid of a light guide. The light reflected by wafer 28 is detected with the aid of a conventional objective 22 provided on an objective turret 20, and fed to a CCD camera 44 via an exchangeable tube lens 40. The image data created in this way are processed in a computation unit, in particular a PC 46, and output in an output device, in particular a monitor 48.

On the bottom side of wafer 28, according to the invention, simultaneously a transmitted-light illumination 52 is provided, with the aid of which the wafer can additionally be illuminated in the transmitted-light mode. This transmitted-light illumination 52 has a transmitted-light source 38, a collector 36 and a filtering means 34. The filtering means enables the light of transmitted-light source 38 to be filtered in the desired IR spectral portion to be used for the transmitted-light illumination of the wafer. To couple-in the IR transmitted light, preferably a light guide 32, such as in the form of an optical fiber bundle is used. After the IR transmitted light has passed an intermediate optics 33, it can be directed onto wafer 28 via a beam-splitting mirror 30. Between beam-splitting mirror 30 and wafer 28 a condenser 29 is usually arranged in combination with a switchable diaphragm. To detect the image of wafer 28, which was created in the IR transmitted-light and incident-light modes, a specialized IR-corrected objective 24 can be used, which is also positioned on objective turret 20 and rotated into the beam path for this purpose. The image can thus be fed to an IR camera 42, and the data generated in this manner can be supplied to a computation unit, such as a PC 46. Here the data can be processed in turn and output via monitor 48.

Focusing of the wafer can be done manually or automatically via an autofocusing system, which is an essential feature to achieve full automation of the whole inspection process.

As can be seen from the FIGURE, the data from the IR incident and transmitted-light inspection and the VIS transmitted-light inspection can be fed to a specialized wavelength selective video double output 41, which is equipped with a visual CCD camera and an IR camera, as shown. In PC 46 the two images can be processed so that they can be shown on monitor 48 either individually or as a combined image. It is the combination of the two imaging methods, in particular, which enables interior elements of the wafer or structures on the underside to be structurally detected and combined with the data obtained from the visual incident-light illumination. This is how the monitoring of production processes of wafers or the other above mentioned samples can be markedly improved.

What is claimed is:

1. An apparatus for inspecting an encapsulated or unencapsulated micro-structured device on a semiconductor substrate, comprising:
    a support for supporting the semiconductor substrate,
    a reflected-light illumination system for illuminating the semiconductor substrate by visible light and infrared light, which lights are reflected from the semiconductor substrate and the micro-structured device as visible reflected light and infrared reflected light,
    a transmitted-light illumination system for illuminating the semiconductor substrate by infrared light simultaneously with the illumination of the reflected-light illumination system, the infrared light having a spectral portion which is transmitted as infrared transmitted light through the semiconductor substrate as if the semiconductor substrate is transparent thereto, wherein the micro-structured device is at least partly non-transparent to the infrared transmitted light,
    a CCD camera for capturing a visual image from the visible reflected-light and an IR camera for capturing an infrared image from the transmitted infrared light and the reflected infrared light simultaneously,
    a computation unit for processing the visual image and the infrared image, to output them as a combined image on a monitor, and
    wherein the apparatus lacks any light source separated from the IR camera by the substrate that generates light, to which the substrate is non-transparent, passing past an external edge of the substrate and captured by the IR camera capturing the image.

2. The apparatus according to claim 1, wherein the reflected-light illumination system comprises a light source and an exchangeable filter means for filtering light.

3. The apparatus according to claim 1, wherein the transmitted-light illumination system comprises a light source and an exchangeable filter means for filtering infrared light.

4. The apparatus according to claim 1, wherein the transmitted-light illumination is coupled in from the underside of the inspected micro-structured device by light guide.

5. The apparatus according to claim 1, wherein the reflected-light illumination system and/or the transmitted-light illumination system comprise switchable diaphragms.

6. The apparatus according to claim 1, wherein the reflected-light illumination system and/or the transmitted-light illumination system comprise an optical fiber.

7. A method for, inspecting an encapsulated or unencapsulated micro-structured device on a semiconductor substrate comprising the following steps:
    supporting the semiconductor substrate by a support,
    illuminating, by a reflected-light illumination system, the semiconductor substrate by visible light and infrared light, which lights are reflected from the semiconductor substrate and the micro-structured device as visible reflected light and infrared reflected light,
    illuminating, by a transmitted-light illumination system, the semiconductor substrate by infrared light simultaneously with the illumination of the reflected-light illumination system, the infrared light having a spectral portion which is transmitted as infrared transmitted light through the semiconductor substrate as if the semiconductor substrate is transparent thereto, wherein the micro-structured device is at least partly non-transparent to the infrared transmitted light,
    capturing a visual image from the visible reflected-light with a CCD camera and capturing an infrared image from the transmitted infrared light and the reflected infrared light with an IR camera simultaneously, processing the visual image and the infrared image to output them as a combined image on a monitor, and wherein the IR camera capturing the infrared image does not capture any light, for which the substrate is non-transparent, passing past an external edge of the substrate after originating from any source separated from the IR camera by the substrate.

8. The method according to claim 7, wherein imaging is carried out with conventional objectives and tube lenses or IR objectives.

9. The method according to claim 8, wherein imaging is carried out via specially corrected IR objectives.

10. The method according to claim 7, wherein focusing of the inspected device is carried out manually or with an autofocusing system.

11. The method according to claim 7, wherein the images of the IR reflected-light illumination and IR transmitted-light illumination are sent by a wavelength-selective video double output to the IR camera and the images of the visible reflected-light illumination are sent by the wavelength-selective video double output to the CCD camera.

12. The apparatus according to claim 1, further comprising a wavelength-selective video double output for sending the images of the visible reflected-light illumination to the CCD camera and of the infrared-light illumination to the IR camera.

* * * * *